(12) United States Patent
Misicka-Kesik et al.

(10) Patent No.: US 11,041,010 B2
(45) Date of Patent: Jun. 22, 2021

(54) HYBRID PEPTIDOMIMETICS FOR USE IN NEUROPATHIC PAIN

(71) Applicants: Uniwersytet Warszawski, Warsaw (PL); Instytut Farmakologii Polskiej Akademii Nauk, Cracow (PL)

(72) Inventors: Aleksandra Misicka-Kesik, Piastow (PL); Ewa Witkowska, Zielonka (PL); Beata Wilenska, Warsaw (PL); Barbara Przewlocka, Cracow (PL); Joanna Mika, Cracow (PL); Joanna Starnowska-Sokol, Miechów (PL); Anna Piotrowska-Murzyn, Zielonki (PL)

(73) Assignees: Uniwersytet Warszawski, Warsaw (PL); Instytut Farmakologii Polskiej Akademii Nauk, Cracow (PL)

( * ) Notice: Subject to any disclaimer, the term of this patent is extended or adjusted under 35 U.S.C. 154(b) by 0 days.

(21) Appl. No.: 16/626,079

(22) PCT Filed: Jul. 3, 2018

(86) PCT No.: PCT/IB2018/054925
§ 371 (c)(1),
(2) Date: Dec. 23, 2019

(87) PCT Pub. No.: WO2019/008515
PCT Pub. Date: Jan. 10, 2019

(65) Prior Publication Data
US 2020/0207827 A1    Jul. 2, 2020

(30) Foreign Application Priority Data
Jul. 3, 2017  (PL) .......................................... 422093

(51) Int. Cl.
*A61K 38/00* (2006.01)
*C07K 14/70* (2006.01)

(52) U.S. Cl.
CPC ............ *C07K 14/702* (2013.01); *A61K 38/00* (2013.01); *C07K 2319/00* (2013.01)

(58) Field of Classification Search
CPC ... C07K 14/702; C07K 2319/00; A61K 38/00
See application file for complete search history.

(56) References Cited

U.S. PATENT DOCUMENTS

2016/0361378 A1    12/2016 Hruby et al.

OTHER PUBLICATIONS

Lee et al. 2010. Design and synthesis of trivalent ligands targeting opioid, cholecystokinin and melanocortin receptors for the treatment of pain. 2010. Bioorganic & Medicinal Chemistry Letters 20 (2010) 4080-4084 (Year: 2010).*
Starowicz et al. 2005. Inhibition of morphine tolerance by spinal melanocortin receptor blockade. Pain 117 (2005) 401-411. (Year: 2005).*
Starowicz, Katarzyna , et al., "Inhibition of morphine tolerance by spinal melanocortin receptor blockade", Pain, Elsevier Science Publishers, Amsterdam, NL, Oct. 1, 2005, vol. 117, pp. 401-411.
Starowicz, Katarzyna , et al., "Modulation of melanocortin-induced changes in spinal nociception by .mu.-opioid receptor agonist and antagonist in neuropathic rats", Neuroreport, Lippincott Williams & Wilkins, UK, Dec. 20, 2002, 2447-2452.
Lee, Yeon Sun, et al., "Design and synthesis and trivalent ligands targeting opioid, cholecystokinin, and melanocortin receptors for the treatment of pain", Bioorganic & Medicinal Chemistry Letters, vol. 20, May 24, 2010, 4080-4084.

* cited by examiner

*Primary Examiner* — James H Alstrum-Acevedo
*Assistant Examiner* — Mercy H Sabila
(74) *Attorney, Agent, or Firm* — Servilla Whitney LLC

(57) ABSTRACT

The invention pertains to novel hybrid peptidomimetics, pharmaceutical composition comprising thereof and use thereof in the treatment of neuropathic pain. The hybrid peptidomimetics according to the invention are comprised of two components: an opioid receptor agonist (OP) and a MC4 receptor antagonist, connected by a linker. The compounds of such a structure will allow to activate opioid receptors with simultaneous blocking of melanocortin type 4 receptors (MC4), which results in enhancing efficiency of the opioid therapy in neuropathic pain.

5 Claims, 13 Drawing Sheets

A Control mice

B CCI mice - mechanical stimulus

C CCI mice - thermal stimulus

A Control mice

B CCI mice - mechanical stimulus

C CCI mice - thermal stimulus

A Control mice

B CCI mice - mechanical stimulus

C CCI mice - thermal stimulus

A Control mice

B CCI mice - mechanical stimulus

C CCI mice - thermal stimulus

A Control mice

B CCI mice - mechanical stimulus

C CCI mice - thermal stimulus

A

B

A CCI mice - intravenous administrations - mechanical stimulus

B CCI mice - intravenous administrations - thermal stimulus

A Control rats

B CCI rats - mechanical stimulus

C CCI rats - thermal stimulus

A Control rats

B CCI rats - mechanical stimulus

C CCI rats - thermal stimulus

A Control rats

B CCI rats - mechanical stimulus

C CCI rats - thermal stimulus

HYBRID PEPTIDOMIMETICS FOR USE IN NEUROPATHIC PAIN

CROSS REFERENCE TO RELATED APPLICATIONS

This is a National Phase entry of International Application No. PCT/IB2018/054925, filed Jul. 3, 2018, which claims priority to Polish Patent Application No. 422093, filed Jul. 3, 2017, the disclosure of which is incorporated herein by reference in its entirety.

FIELD OF THE INVENTION

The invention pertains to novel hybrid peptidomimetics, a pharmaceutical composition comprising thereof and use thereof in the treatment of neuropathic pain. Peptidomimetics according to the invention comprise two components: an opioid receptor agonist (OP) and melanocortin type 4 receptor antagonist (MC4) connected by a linker.

PRIOR ART

Neuropathic pain is a type of chronic pain resulting from an injury of a nervous tissue. The difficulties in its treatment consist of the lack of suitable potent and long-acting drugs, since opioid drugs employed successfully in acute pain lose their analgesic efficiency in neuropathic pain. This effect is explained as a result of excessive, pathological activation of endogenic pronociceptive systems due to the injury. Activity of such systems oppose the analgesic activity of opioid drugs, hence their efficiency is reduced. A publication by Sandkühler, J. Physiol. Rev. 89, 707-58, 2009, notices that the axial symptoms of neuropathic pain-allodynia and hyperalgesia-result from permanent activation of the pronociceptive systems. In a review by Nickel, F. T. et al., Eur. Neuropsychopharmacol. 22, 81-91, 2012 a number of injury-activated pronociceptive systems are described, with the most interesting being a melanocortin system and a melanocortin type 4 receptor (MC4). Peptides that activate this receptor are derived from proopiomelanocortin, a prohormone from which opioid peptides such as beta-endorphin also originate. (Tao, Y.-X., Endocr. Rev. 31, 506-43, 2010). In this case, an injury-induced activation of opioid systems with analgesic activity is connected with simultaneous activation of pronociceptively acting peptides derived from the same prohormone.

The MC4 receptors are the only melanocortin receptors which are expressed in the central nervous system, and apart from other functions, they are involved in processing of pain signalization. The publication by Beltramo, M. et al., Mol. Brain Res. 118, 111-118, 2003 discloses the fact that activation of these receptors results in pain, and their blockade leads to analgesia. MC4 and opioid receptors are coexpressed in the spinal cord, indicating potential interactions between the systems (Tao, 2010). In previous studies (Starowicz, K. et al. Pharmacol. Reports 61, 1086-95, 2009) increase in the synthesis of MC4 receptor in the spinal cord was shown following a nerve injury in the rat model of neuropathic pain. Moreover, the administration of antagonists of that receptor described by Hruby et al., J. Med. Chem. 38, 3454-61., 1995 led to analgesia and enhanced activity of morphine. Further, in other studies concerning MC4 receptor antagonists, Starowicz. K. et al., Pain 117, 401-11, 2005 has shown reduction of morphine tolerance development after their simultaneous subarachnoid administration in a rat.

The review by Bednarek et al., Expert Opin. Ther. Patents, 14, 327-336, 2004 describes known melanocortin MC4 receptor antagonists. WO2001052880 discloses cyclic peptides as effective antagonists of the human melanocortin MC4 receptor. Among the compounds disclosed, the compound MBP-10: cyclo[CO—$CH_2$—$CH_2$—CO-D-Nal(2') -Arg-Trp-Lys]-$NH_2$ is present for uses in the treatment of i.a. anorexia and bulimia. WO2003006620 discloses melanocortin receptor antagonist derivatives SHU9119 with Ser(Bzl) substitution at His and Phe(4Cl) at Phe. The publication WO2003061660 discloses melanocortin receptor agonists effective in the treatment of obesity, diabetes and sexual disfunctions in women. The application WO2013138340 describes analogues of melanocortin with enhanced activity and transport. It is also indicated that melanocortin receptor antagonists could serve as regulators of delta opioid receptor functions and by indirect inhibition of melanocortin system enhance opioid effects.

Hybrid peptides raise growing interest as potential pharmacological agents. Exemplary hybrid peptides with therapeutic properties were described in the publication by Bhat V. K et al., Biochem Pharmacol. 85, 1655-62, 2013. The patent application US20120264685A1 discloses also novel short-chain peptidomimetics which act simultaneously as GLP-1 receptor and glucagon receptor agonists.

Although appearance of neuropathic pain accompanies many diseases, no effective means for its control have been developed so far. The present invention is aimed at development of novel peptidomimetics with analgesic properties, which could enhance efficiency of the opioid therapy in neuropathic pain.

Subject Matter of the Invention

The above-mentioned object was achieved by the development of novel peptidomimetics with analgesic properties, intended for use in neuropathic pain. The peptidomimetics according to the invention comprise two components: an opioid receptor agonist (OP) and an MC4 receptor antagonist, connected by a linker. Compounds of such a structure will allow to activate opioid receptors with simultaneous blocking of MC4 receptors, leading to enhanced efficiency of the opioid therapy in neuropathic pain.

The invention provides a compound of the general formula:

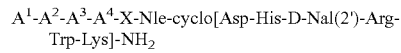
$A^1$-$A^2$-$A^3$-$A^4$-X-Nle-cyclo[Asp-His-D-Nal(2')-Arg-Trp-Lys]-$NH_2$ wherein:
$A^1$ is a Tyr, DMT (2,6-dimethyltyrosine), or N-Me-Tyr (N-methyltyrosine) residue,
$A^2$ is a D-Ala, D-Thr, D-Ser, D-Leu, D-Arg, D-Lys, or D-Pro residue,
$A^3$ may be absent or is a Gly or Phe residue,
$A^4$ is a Phe or Trp residue,
X is —NH—$(CH_2)_n$—CO—, or —NH—$(CH_2)_n$—CO—NH—$(CH_2)_m$—CO—, wherein n and m are integers from 1 to 8, or is —(Pro-Gly)$_z$—; wherein z is an integer from 1 to 4;
or a pharmaceutically acceptable salt or hydrate thereof.

Preferably, the compound according to the invention is selected from the group comprising the following compounds:
1. Tyr-D-Ala-Gly-Phe-X-Nle-cyclo[Asp-His-D-Nal(2')-Arg-Trp-Lys]-$NH_2$
2. Tyr-D-Thr-Gly-Phe-X-Nle-cyclo[Asp-His-D-Nal(2')-Arg-Trp-Lys]-$NH_2$ 3. Tyr-D-Leu-Gly-Phe-X-Nle-cyclo[Asp-His-D-Nal(2')-Arg-Trp-Lys]-NH$_2$
4. Tyr-D-Ser-Gly$^3$-Phe$^4$—X-Nle-cyclo[Asp-His-D-Nal(2')-Arg-Trp-Lys]-NH$_2$
5. DMT-D-Ala-Gly-Phe-X-Nle-cyclo[Asp-His-D-Nal(2')-Arg-Trp-Lys]-NH$_2$
6. DMT-D-Thr-Gly-Phe-X-Nle-cyclo[Asp-His-D-Nal(2')-Arg-Trp-Lys]-NH$_2$
7. DMT-D-Leu-Gly-Phe-X-Nle-cyclo[Asp-His-D-Nal(2')-Arg-Trp-Lys]-NH$_2$
8. DMT-D-Ser-Gly-Phe-X-Nle-cyclo[Asp-His-D-Nal(2')-Arg-Trp-Lys]-NH$_2$ wherein X is —NH—(CH$_2$)$_n$—CO—; or —NH—(CH$_2$)$_n$—CO—NH—(CH$_2$)$_m$—CO—.

In a preferred embodiment, the compound according to the invention is: Tyr-D-Ala-Gly-Phe-NH—(CH$_2$)$_5$—CO-Nle-cyclo[Asp-His-D-Nal(2')-Arg-Trp-Lys]-NH$_2$ or Tyr-D-Ala-Gly-Phe-NH—(CH$_2$)$_5$—CO—NH—(CH$_2$)$_5$—CO-Nle-cyclo[Asp-His-D-Nal(2')-ArgTrp-Lys]-NH$_2$.

The invention provides also a pharmaceutical composition comprising as an active ingredient the compound according to the invention.

The invention pertains also to medicinal uses of the compound according to the invention, in particular for use in the treatment of neuropathic pain.

DESCRIPTION OF THE FIGURES

The invention was presented in detail in the working examples also in reference to the appended figures of the drawing, wherein.

DETAILED DESCRIPTION OF THE INVENTION

Figure 1:
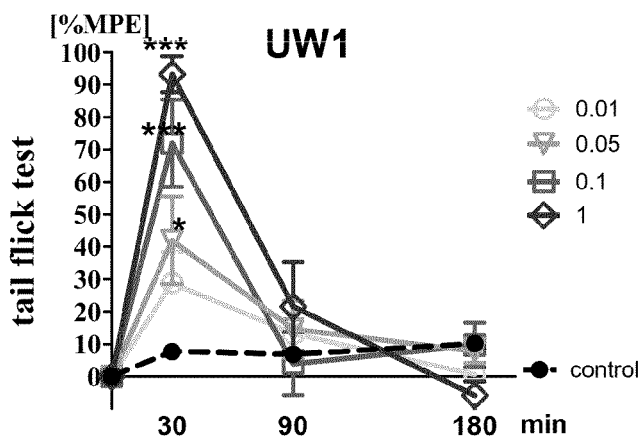
FIGS. 1-7 are graphs-results of the studies on the influence of intrathecal administration of the parent compounds (UW1 (FIG. 1), SHU9119 (FIG. 2)), the hybrid peptidomimetics according to the invention (UW3 (FIG. 4) and UW5 (FIG. 6)), and the reference compounds (UW2 (FIG. 3), UW4 (FIG. 5), UW6 (FIG. 7)) on an acute pain threshold in healthy mice (control mice) (A) and a sensitivity to a mechanical stimulus (B) (von Frey test) and a thermal stimulus (C) (cold plate test) threshold in mice CCI compared to a control group receiving water for injection.
Figure 1:
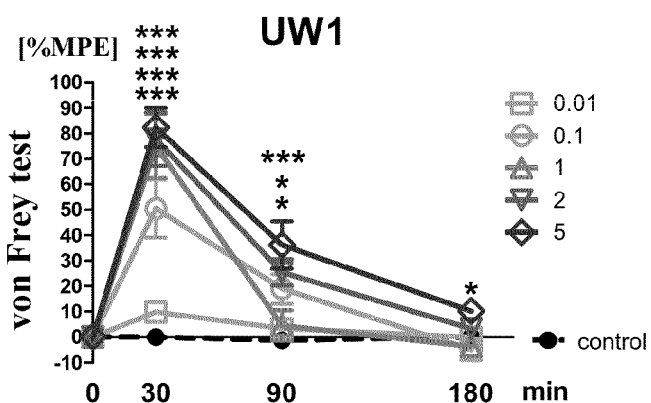
Figure 1:
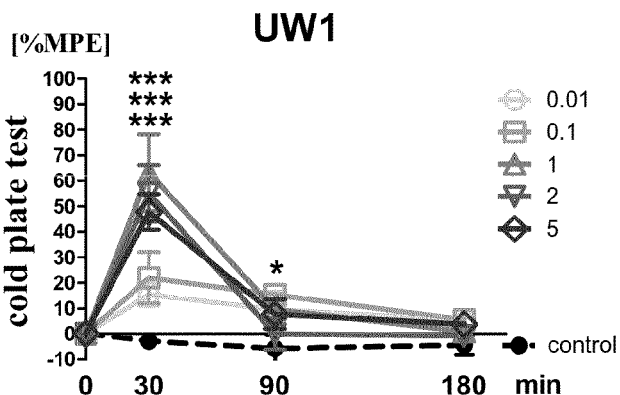

The hybrid peptidomimetics according to the invention are characterized in that they comprise two components responsible for their biological activity-an opioid receptor agonist and MC4 receptor antagonist, connected by a linker. The formula of the particularly preferred peptidomimetics according to the invention, which include enkephalin analogue (an opioid peptide of the formula Tyr-Gly-Gly-Phe-Leu-OH) of the formula Tyr-D-Ala-Gly-Phe-NH$_2$ (UW1) as an opioid agonist and SHU9119 (a peptide of the formula Ac-Nle-cyclo[Asp-His-D-Nal(2')-Arg-Trp-Lys]-NH$_2$, reported in Hruby et al., 1995, as an MC4 receptor antagonist, is shown below:

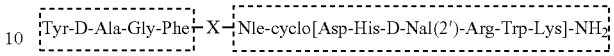

opioid agonist-linker-MC4 receptor antagonist, wherein X is a linker adapted to provide suitable and simultaneous action of both biologically active components. As indicated above, the particularly preferred linkers are —NH(CH$_2$)$_n$—CO— (also referred to in the present specification as—εAhx—), or —NH—(CH$_2$)$_n$—CONH—(CH$_2$)$_m$—CO— (also referred to in the present specification as—εAhx-εAhx—).

Selection of a linker is crucial for maintaining high biological activity of the compound according to the invention on the therapeutic level. The inventors have synthesized the reference hybrid peptides, denoted as UW2, UW4 and UW6, which have differed from compounds according to the invention in a linker, and analgesic properties thereof were much worse, as it was shown in Examples below. Sequences of the reference compounds are shown below:

UW2: Tyr-D-Ala-Gly-Phe-D-Ala-Nle-cyclo[Asp-His-D-Nal(2')-Arg-Trp-Lys]-NH$_2$;
UW4: Tyr-D-Ala-Gly-Phe-β-Ala-Nle-cyclo[Asp-His-D-Nal(2')-Arg-Trp-Lys]-NH$_2$;
UW6: Tyr-D-Ala-Gly-Phe-4AMB-Nle-cyclo[Asp-His-D-Nal(2')-Arg-Trp-Lys]-NH$_2$.

As reference compounds, the enkephalin derivative, denoted UW1, with the following structure: UW1: Tyr-D-Ala-Gly-Phe-NH$_2$, and SHU9119, i.e. the parent compounds which compose the hybrid peptidomimetics, were used.

The opioid agonist component, i.e. the enkephalin derivative, can be subjected to further modifications to obtain even better activity of hybrid peptidomimetics according to the invention. It is particularly preferred to substitute a tyrosine residue at a position 1 (Tyr$^1$) with a L-2,6-dimethyltyrosine (DMT) residue. Other modifications are also possible, e.g. replacing a D-alanine residue (D-Ala) at a position 2 with a D-treonine residue (D-Thr) or D-serine (D-Ser) and/or glycine (Gly) at a position 3 with phenylalanine (Phe).

In the result of the conducted studies it was found that hybrid peptidomimetics according to the invention, while acting at the same time upon two components of the analgesic effect, provide simultaneous effect on both systems (on analgesic activation and nociceptic inhibition) within the same fragment of the nociceptive pathways, resulting in multiplication of the pain inhibition process at the ascending tracts of the nervous system. Administration of corresponding components of the hybrid alone does not produce such an effect due to different distribution of each of them which leads to analgesic effect dissipation. Combining the opioid agonist and MC4 receptor antagonist via a proper linker into one hybrid peptidomimetic results in the active components of the peptidomimetic reaching simultaneously the target activity site, i.e. the two receptors. In the case of administering each of the components separately, the effect would be impossible to obtain, due to the important role of additional factors, such as the rate of absorption of particular components, their metabolism and the rate of clearance from the patient's circulation, the factor mentioned would prevent the components from reaching the receptors at the same time, and thus preclude their simultaneous activities.

Owing to the structure of hybrid peptidomimetics according to the invention it is possible to obtain a more potent positive effect of the therapy of neuropathic pain, which affects every fifth European, and which, due to ageing of the society, requires more and more frequently a safe treatment. As it is shown in Examples below, by comparing $ED_{50}$ values, i.e. dosages at which a half (50%) of the maximum effect of a given substance is reached or at which 50% of the individuals studied exhibit the expected effect, the hybrid peptidomimetics according to the invention could be employed at the very low dosages. Due to this, they should not result in any adverse effects, which is an extremely essential requirement in application of such a drug, considering chronicity of neuropathic pain.

According to the invention, the hybrid peptidomimetics developed by the present inventors could be prepared in the form of salts and hydrates by processes known in the art. The term "salts" relates to pharmaceutically acceptable acid addition salts with amine or guanidine groups of the hybrid peptidomimetics according to the invention. The acid addition salts include, e.g., both salts of mineral acids, such as, e.g., hydrochloric or sulfuric acid, and salts of organic acids, such as acetic acid or oxalic acid.

Furthermore, the invention provides a pharmaceutical composition for the treatment of neuropathic pain comprising the active component in the form of the hybrid peptidomimetic according to the invention and pharmaceutically acceptable auxiliary substances. Examples of the auxiliary substances are carriers, which include large, slowly metabolized macroparticles, such as proteins, polypeptides, liposomes, polysaccharides, polylactic acids, polyglycolic acids, polymeric amino acids, copolymers of amino acids and inactive virus molecules. Liquids, such as water, normal saline, glycerol and ethanol could be the alternative carriers. In pharmaceutical compositions according to the invention, there may also be present other auxiliary substances, such as humidifying and emulsifying agents or pH regulators, which aid formulation of the active ingredient into the required dosage form.

Definitions

Unless defined otherwise, the terms applied in the present description enjoy meanings generally clear for the persons skilled in the art.

The term agonist means a compound which, by binding a receptor, elicits a biological response in a cell. An example of the agonist is the opioid agonist UW1: Tyr-D-Ala-Gly-Phe-NH$_2$. The term antagonist means a compound, which binds to a receptor, but does not elicit a biological response. The exemplary MC4 antagonist is SHU9119:

Ac-Nle-cyclo[Asp-His-D-Nal(2')-Arg-Trp-Lys]-NH$_2$.

Within the present application, the standard designations of amino acids are used, and chirality is denoted in the cases of D amino acids only. Other designations used herein are presented below:
4AMB: 4-aminomethylbenzoic acid;
Ac: acetyl group;
Boc: tert-butoxycarbonyl group;
Bom: benzyloxymethyl group
DCM: dichloromethane;
DIPEA: N,N-diisopropylethylamine;
DMF: dimethylformamide;
DMT: 2,6-dimethyl-L-tyrosine;
Fmoc: 9-fluorenylmethoxycarbonyl group;
For: formyl group
HBTU: (0-benzotriazol-1-yloxy)-N—N—N'—N'-tetramethyl-uronium hexafluorophosphate;
Nal(2'): 3-(2'-naphthyl)-L-alanine;
TBTU: (0-benzotriazol-1-yloxy)-N—N—N'—N'-tetramethyl-uronium tetrafluoroborate;
tBu: tert-butyl group
Tos: tosyl (p-toluenesulfonyl) group
MBHA resin: 4-methylbenzhydrylamine resin;
β-Ala: 3-aminopropanoic acid;
εAhx: 6-aminohexanoic acid;

EXAMPLES

Example 1: Synthesis of the Hybrid Peptides and ESI MS Analysis

Synthesis

All hybrid peptides, both compounds according to the invention (UW3 and UW 5), and reference compounds (UW2, UW4 and UW6), were synthesized in the same way, according to the following procedure.

Synthesis of the peptides was carried out on the polymeric MBHA support with a loading of 0.27 mmol/g. The synthesis utilized the amino acid derivatives: Boc-L-Lys(Fmoc)-OH, Boc-L-Trp(For)-OH, Boc-L-Arg(Tos)-OH, Boc-D-Nal(2')—OH, Boc-L-His(Bom)-OH, Boc-L-Asp(OFm)—OH, Boc-L-Nle-OH, Boc-L-Phe-OH, Boc-Gly-OH, Boc-D-Ala-OH, Boc-L-Tyr(tBu)—OH. The derivatives of suitable amino acids were used for the preparation of a linker: Fmoc-εAhx-OH, Boc-D-Ala-OH, Boc-β-Ala-OH or Fmoc-4AMB-OH. To remove Boc protection from the α-amino functionalities, a 50% solution of trifluoroacetic acid in DCM was used, while a 30% solution of piperidine in DMF was used to remove Fmoc protection. The coupling reactions were conducted mainly by a carbodiimide process by use of N,N'-diizopropylcarbodiimide (DIC) as a coupling reagent in the presence of N-hydroxybenztriazole (HOBt) with a 3-fold molar excess of the reagents based on a degree of loading of the MBHA resin. The reaction was carried out for 2 hours. Attachment efficiency of every amino acid residue was monitored by the ninhydrin (Kaiser) test for the presence of free amine groups. If free amino groups were detected after coupling, the coupling reaction was repeated with use of HBTU or TBTU as the coupling reagent in the presence of HOBt and DIPEA. To form the lactam ring, protections of the functional groups in the side chains of aspartic acid (OFm) and lysine (Fmoc) residues were removed by use of a 30% solution of piperidine in DMF, followed by cyclization by the carbodiimide method for 4 hours. The cyclization was repeated until the negative result of the ninhydrin test (the absence of free amine groups) was obtained. In the final step of the cyclization (at 4th or 5th repeat) the uronium salt method was applied. The cyclization reaction lasted usually 16-20 hours. After the cyclization was completed, the peptide synthesis was continued. The removal of the peptide from the resin and removal of the remaining protection from the functional groups in the amino acids side chains was carried out in the reaction with liquid hydrogen fluoride in the presence of anisole at 0° C. for 60 minutes.

The consecutive steps of the synthesis are shown below:
I. Synthesis of SHU9119 fragment on a polymeric support (Boc-Nle-Asp-His-D-Nal(2')-Arg-Trp-Lys-MBHA);

II. Cyclization of the peptide chain (formation the lactam ring between Asp[7] and Lys[12] residues);
III. Attachment of the compound X;
IV. Synthesis of a tetrapeptide analogue of the enkephalin fragment (Tyr-D-Ala-Gly-Phe-NH$_2$) or its analogue, as an opioid agonist;
V. Removal of the peptide from the resin with simultaneous removal of protecting groups with liquid HF;
VI. Purification of the peptides by RP-HPLC;
VII. Confirmation of the structure of hybrid peptides by mass spectrometry.

The obtained products can be converted in a pharmaceutically acceptable salt by conventional means.

Analysis and Purification

Analysis and purification of the obtained hybrid peptides was conducted by RP HPLC on the KNAUER liquid chromatograph. Mass spectra were registered on the Shimadzu LC-MS mass spectrometer provided with an ESI ion source (electrospray), ion trap and time-of-flight analyzer. Analyses were carried out in the positive ion mode.

Analytical Data

The analytical data of the compounds obtained are presented below.

Peptidomimetic UW2 (the Reference Compound)
Tyr-D-Ala-Gly-Phe-D-Ala-Nle-cyclo[Asp-His-D-Nal(2')-Arg-Trp-Lys]-NH$_2$
$C_{78}H_{100}N_{20}O_{14}$ Mol. wt. 1540.8 g/mol
ESI MS Analysis Result

| UW2 | | |
|---|---|---|
| Ion | m/z calculated [u] | m/z measured [u] |
| [M + 2H]$^{2+}$ | 771.4 | 771.4 |
| [M + 3H]$^{3+}$ | 514.6 | 514.6 |

Peptidomimetic UW3 (the Compound According to the Invention)
Tyr-D-Ala-Gly-Phe-εAhx-Nle-cyclo[Asp-His-D-Nal(2')-Arg-Trp-Lys]-NH$_2$
$C_{81}H_{106}N_{20}O_{14}$ Mol. wt. 1583.8 g/mol
ESI MS Analysis Result

| UW3 | | |
|---|---|---|
| Ion | m/z calculated [u] | m/z measured [u] |
| [M + 2H]$^{2+}$ | 792.4 | 792.4 |
| [M + 3H]$^{3+}$ | 528.6 | 528.9 |

Peptidomimetic UW4 (the Reference Compound)
Tyr-D-Ala-Gly-Phe-β-Ala-Nle-cyclo[Asp-His-D-Nal(2')-Arg-Trp-Lys]-NH$_2$
$C_{78}H_{100}N_{20}O_{14}$ Mol. wt. 1540.8 g/mol
ESI MS Analysis Result

| UW4 | | |
|---|---|---|
| Ion | m/z calculated [u] | m/z measured [u] |
| [M + 2H]$^{2+}$ | 771.4 | 771.4 |
| [M + 3H]$^{3+}$ | 514.6 | 514.6 |

Peptidomimetic UW5 (the Compound According to the Invention)
Tyr-D-Ala-Gly-Phe-εAhx-εAhx-Nle-cyclo[Asp-His-D-Nal(2')-Arg-Trp-Lys]-NH$_2$
$C_{87}H_{117}N_{21}O_{15}$ Mol. wt. 1697 g/mol
ESI MS Analysis Result

| UW5 | | |
|---|---|---|
| Ion | m/z calculated [u] | m/z measured [u] |
| [M + 2H]$^{2+}$ | 849.5 | 849.5 |
| [M + 3H]$^{3+}$ | 566.6 | 566.6 |

Peptidomimetic UW6 (the Reference Compound)
Tyr-D-Ala-Gly-Phe-4AMB-Nle-cyclo[Asp-His-D-Nal(2')-Arg-Trp-Lys]-NH$_2$
$C_{83}H_{102}N_{20}O_{14}$ Mol. wt. 1603.8 g/mol
ESI MS Analysis Result

| UW6 | | |
|---|---|---|
| Ion | m/z calculated [u] | m/z measured [u] |
| [M + 3H]$^{3+}$ | 535.60 | 535.60 |

Example 2: Preclinical Studies on the Mouse and Rat Model of Neuropathic Pain

The analgesic efficiency of the compounds according to the invention was tested in the first stage of the preclinical studies on a mouse model of neuropathic pain. This stage was used to select hybrid peptidomimetics with the most potent activity, and therefore to obtain very important information on which of the compounds studied exhibited the requested potent biological effect. The reference compounds, which failed to reach the required potency of the analgesic effect (UW2, UW4 and UW6), did not pass to the second stage of pharmacological studies. This study stage decided on the second stage of additional research conducted on mice and rats, to which two hybrid peptidomimetics UW3 and UW5 according to the invention with potent activity and their parent compounds for the comparison purposes: UW1, SHU9119 and enkephalin, were selected.

Mouse Studies

Albino Swiss mice were subjected to a loose unilateral ligation of the right sciatic nerve (a chronic constriction injury, CCI) according to the model developed by Bennett and Xie, Pain 33, 87-107, 1998. Seven days after the procedure, behavioral tests were conducted to demonstrate hyperalgesia due to neuropathy: the von Frey test to measure hypersensitivity to tactile stimuli, and the cold plate test to measure hypersensitivity to thermal stimuli. At days 7-14 from the CCI procedure, when the most potent and permanent hypersensitivity level is obtained, behavioral tests were conducted at 30, 90 and 180 minutes after intrathecal administration of hybrid compounds in selected doses. The tests permitted to determine the analgesic efficiency of the novel compounds in the model of neuropathic pain. In the control mice (due to the absence of hypersensitivity, which characterizes neuropathic pain) at the same time points, a test of tail flick was conducted to determine pain threshold in the acute pain after intrathecal administration of the hybrid peptidomimetics.

Discussion of the Results of the First Stage Study on Mice

Figure 2:
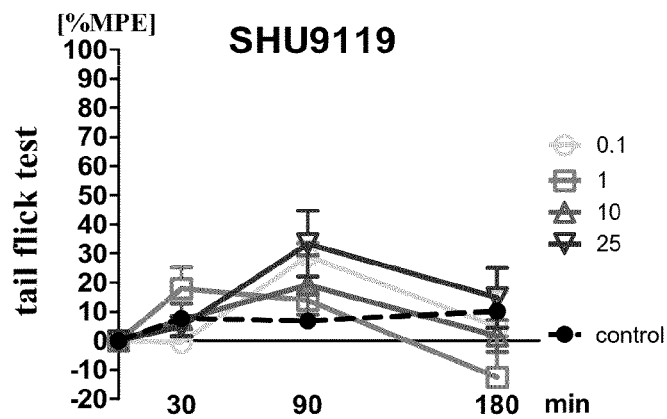
Figure 2:
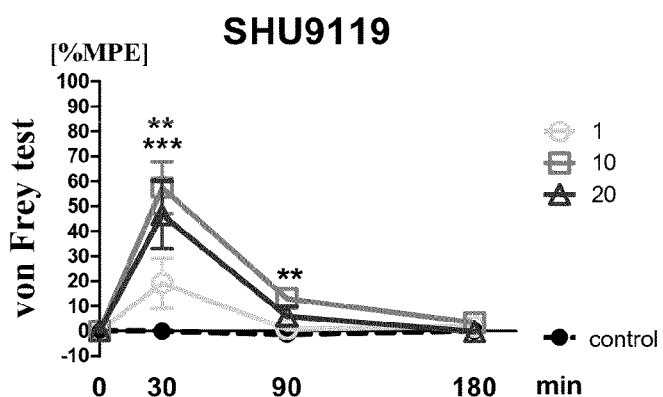
Figure 2:
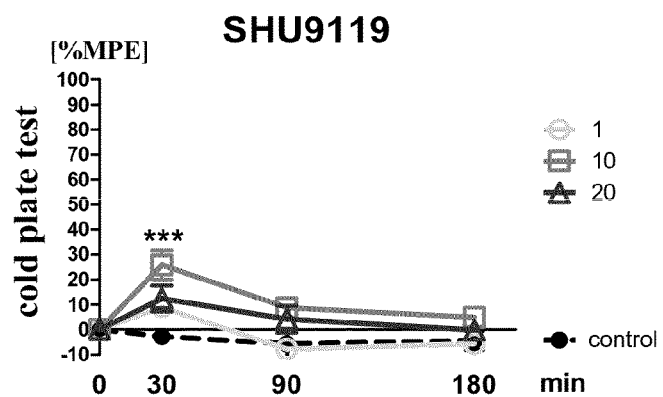
Figure 3:
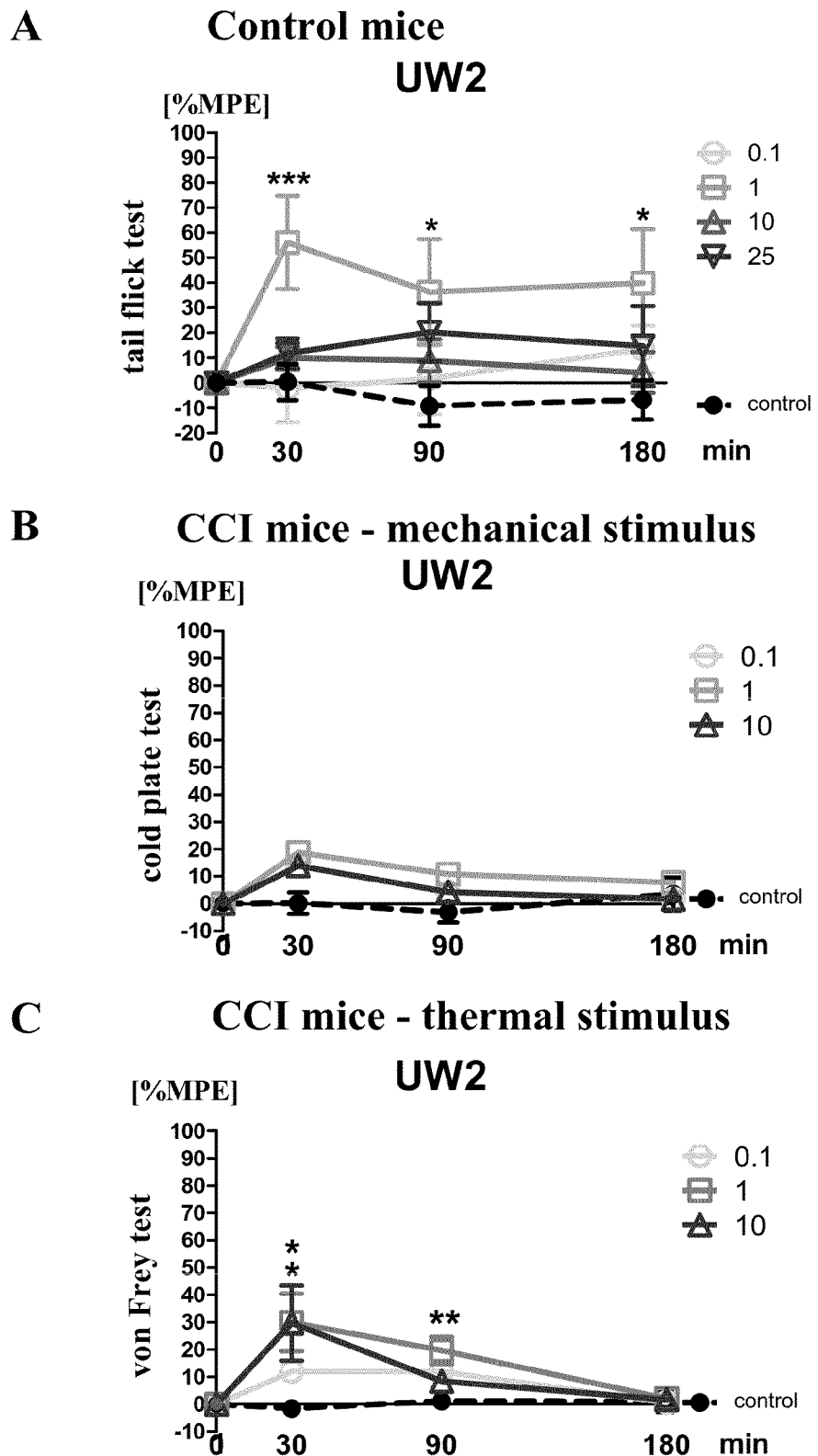
Figure 4:
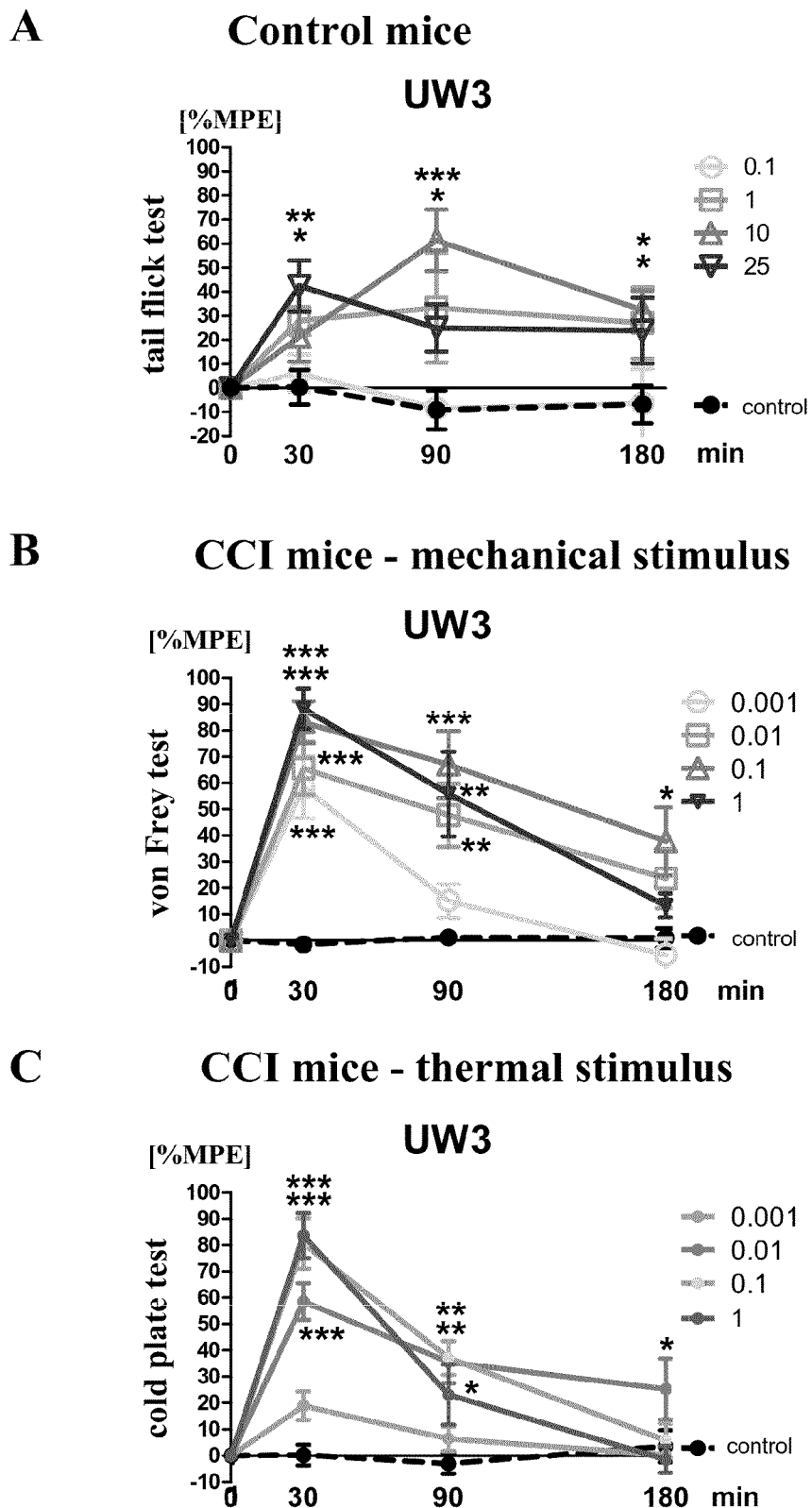
Figure 5:
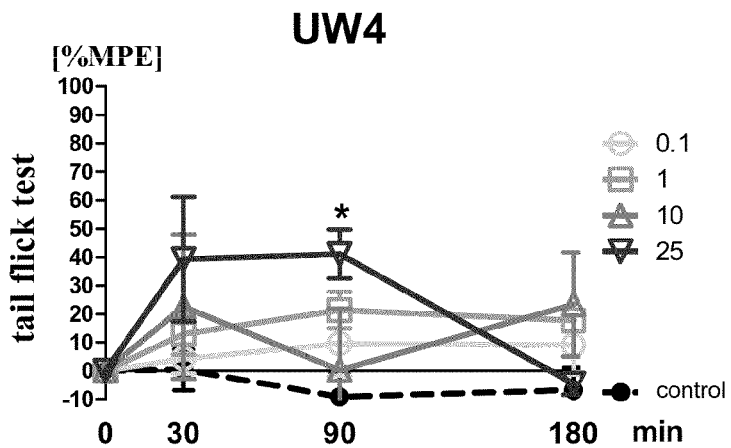
Figure 5:
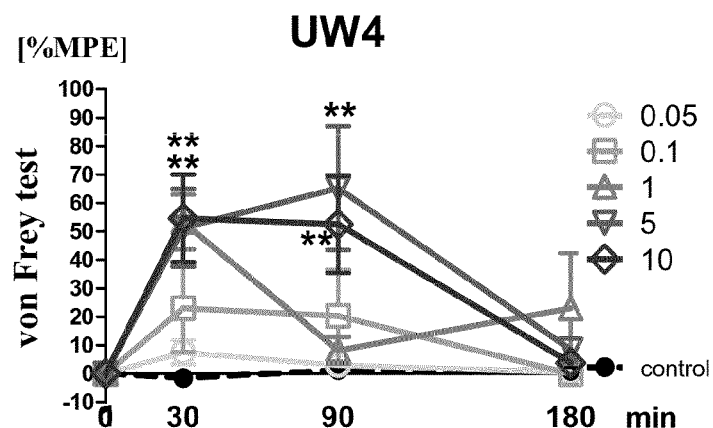
Figure 5:
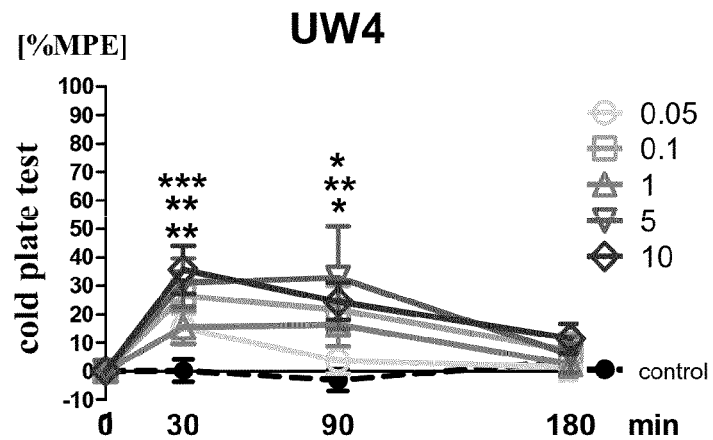
Figure 6:
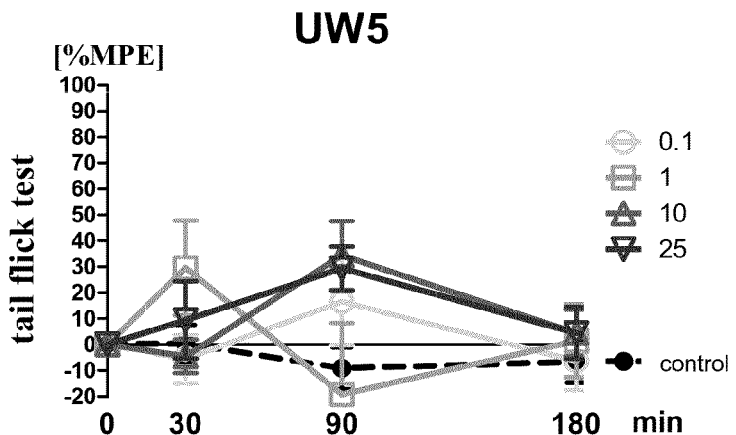
Figure 6:
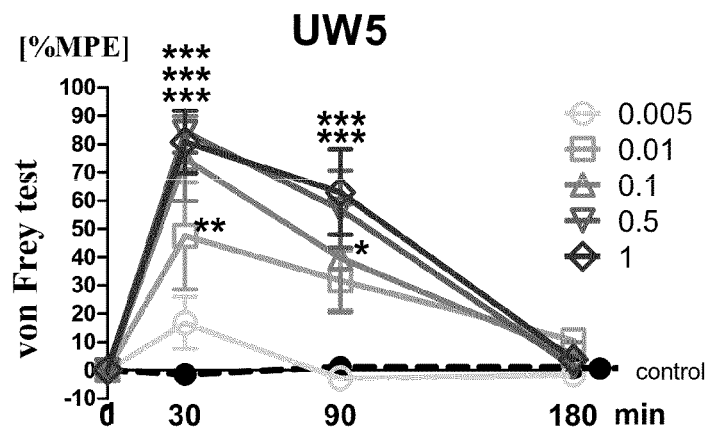
Figure 6:
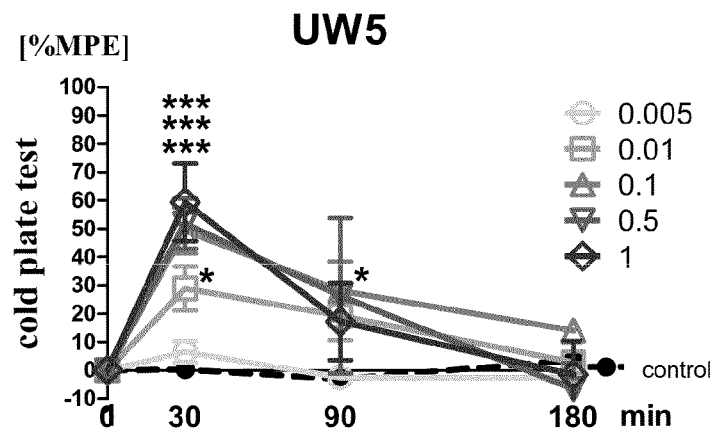
Figure 7:
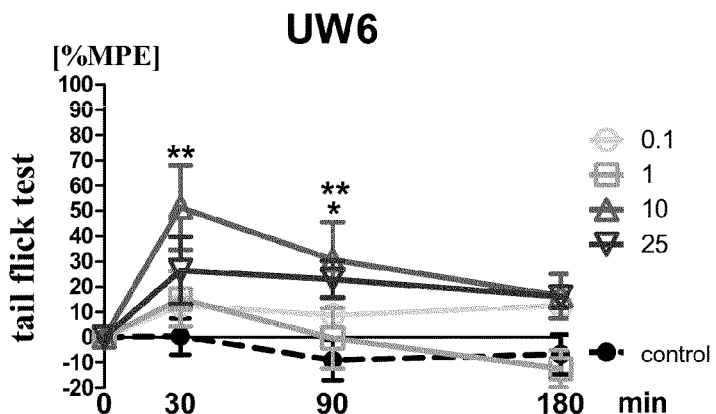
Figure 7:
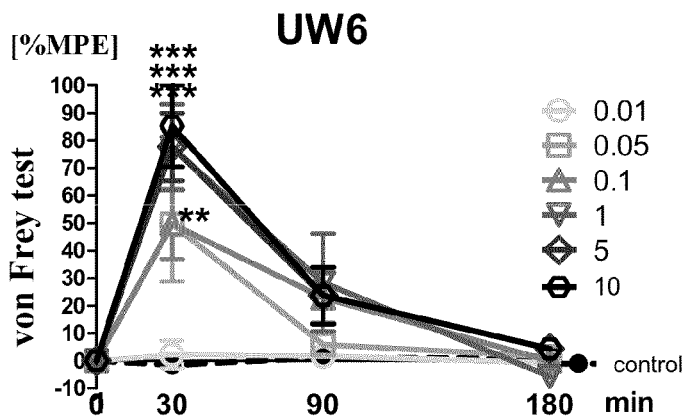
Figure 7:
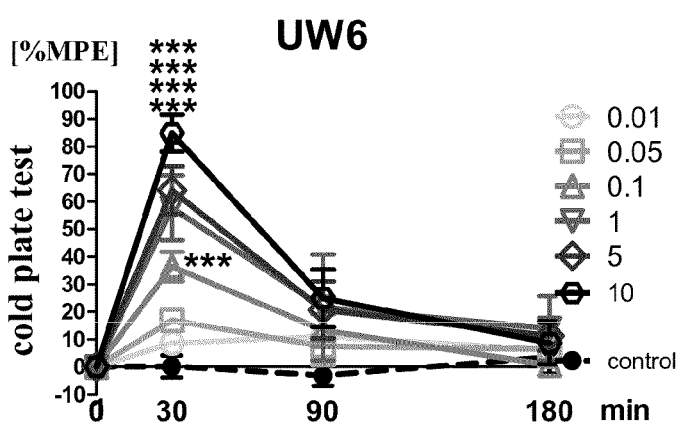

The analgesic activity after intrathecal administration of the hybrid peptidomimetics in control mice and in the mouse model of neuropathic pain is shown in FIGS. 1-7. The activity curves of the standard parent compounds (the opioid receptor agonist: UW1 and MC4 receptor antagonist: SHU9119) are shown in FIGS. 1 and 2. Both parent compounds show activity in control mice, but their activity in neuropathic pain is weakened in both or at least one hypersensitivity determining test. However, the hybrid peptidomimetics UW3, UW5 according to the invention (FIGS. 4 and 6, respectively) with limited analgesic efficiency in healthy mice are characterized with higher analgesic efficiency in mice with neuropathy symptoms, which confirms rightness of the hypothesis on activity of the hybrids, and provides high efficiency of the compounds in neuropathic pain.

Discussion of the Results of the Second Stage Study on Mice

Figure 8:
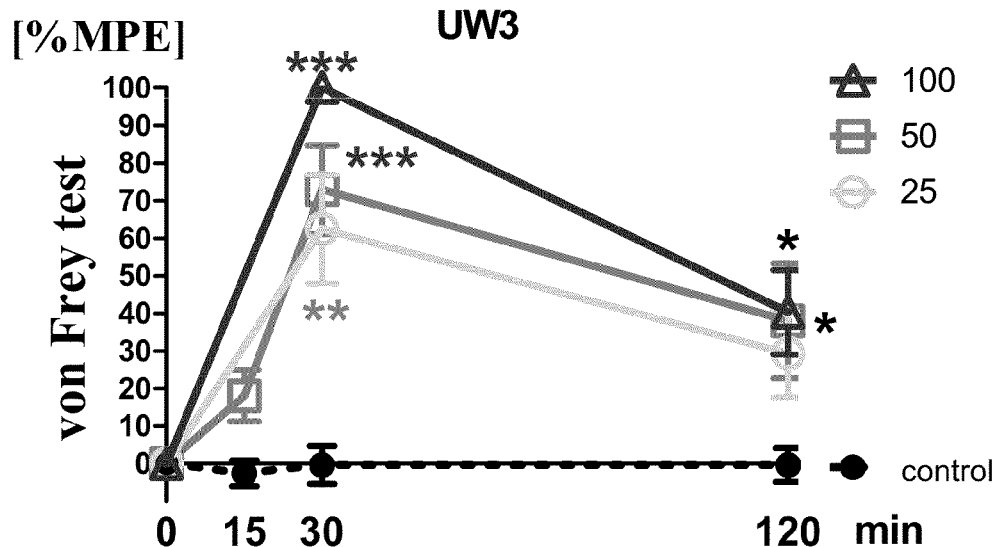
FIG. 8-9 are graphs-results of the studies on the influence of intravenous administration of the hybrid peptidomimetics according to the invention (UW3 (FIG. 8), UW5 (FIG. 9)) on a sensitivity to a mechanical stimulus (A) (von Frey test) and a thermal stimulus (B) (cold plate test) threshold in CCI mice compared to a control group receiving water for injection.
Figure 8:
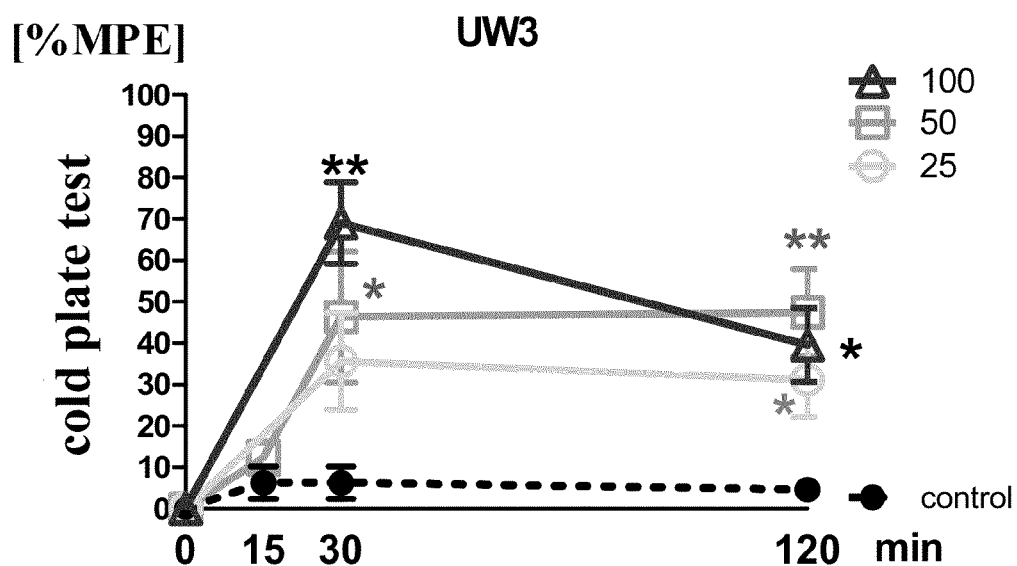
Figure 9:
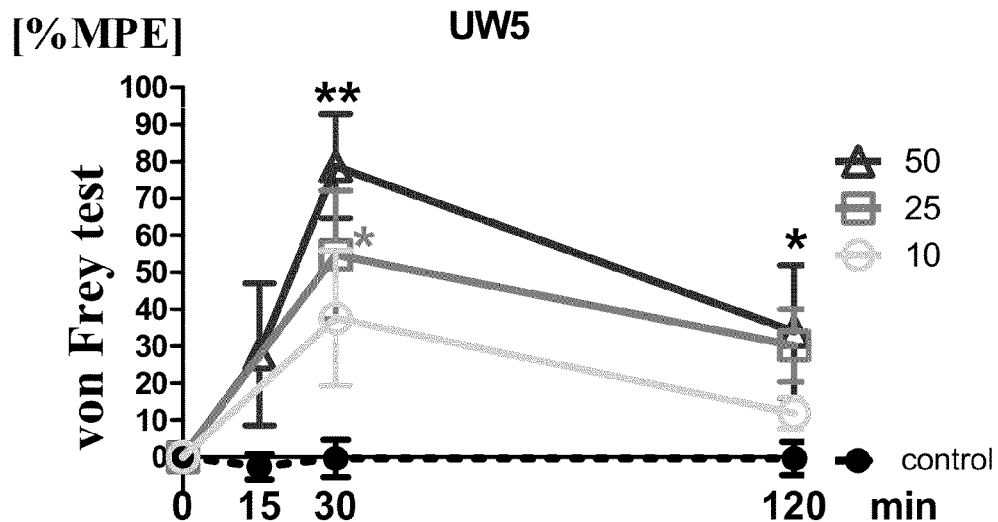
Figure 9:
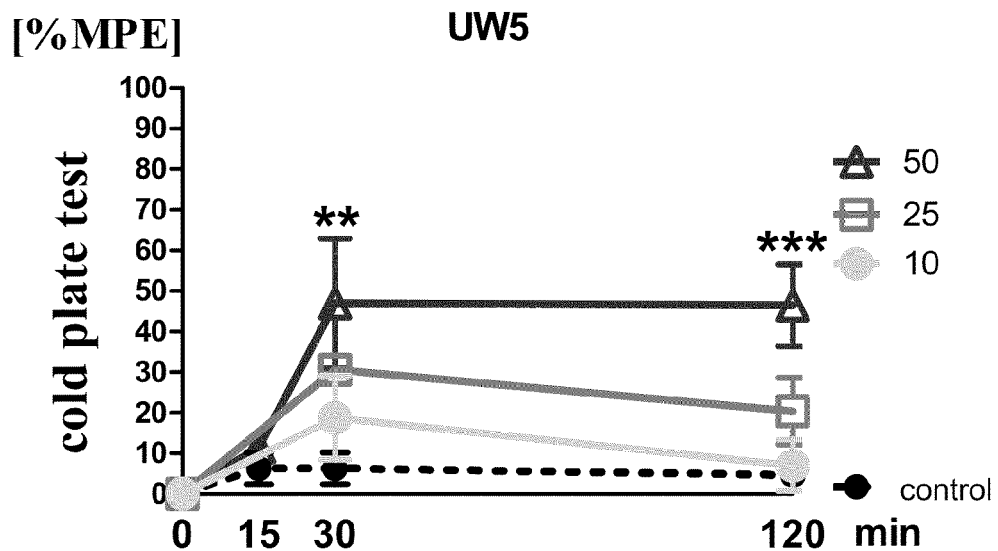
Figure 10:
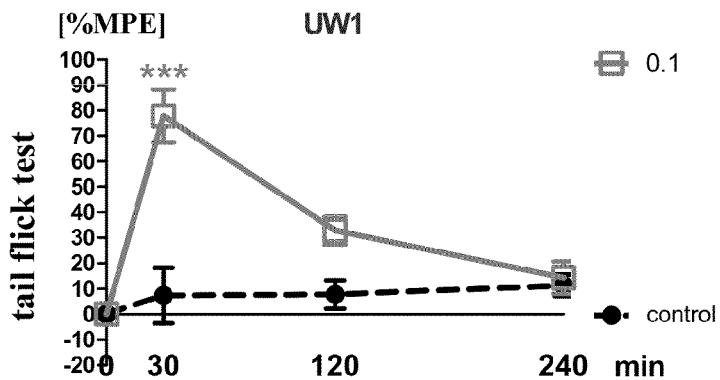
FIG. 10-13 are graphs-results of the studies on the influence of administration of the parent compounds (UW1/enkephalin (FIG. 10), SHU9119 (FIG. 11) and the hybrid peptidomimetics according to the invention (UW3 (FIG. 12), UW5 (FIG. 13)) at a dose of 0.1 μg/5 μl/rat on an acute pain threshold in healthy rats (A) and a sensitivity to a mechanical stimulus (B) (von Frey test) and mechanical stimulus (C) (cold plate test) threshold in CCI rats compared to a control group receiving water for injection.
Figure 10:
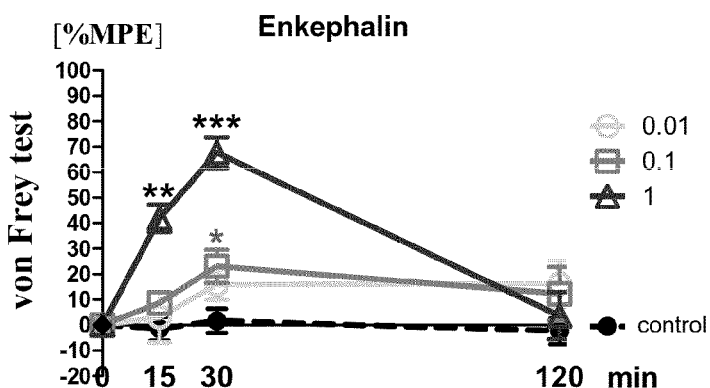
Figure 10:
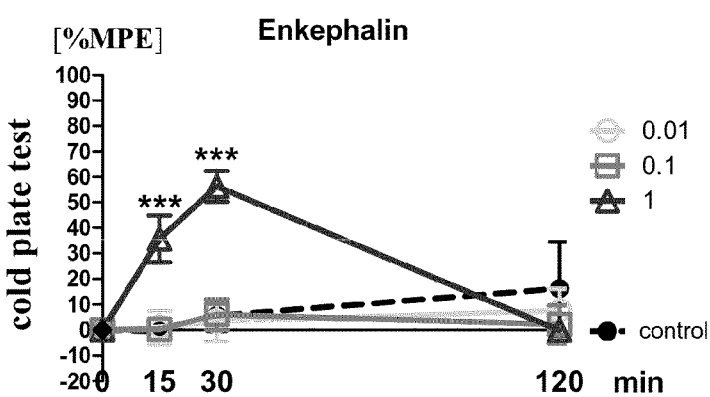
Figure 11:
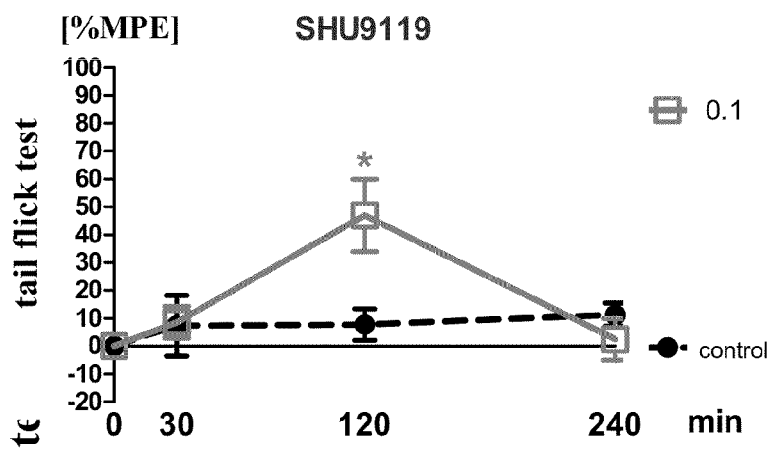
Figure 11:
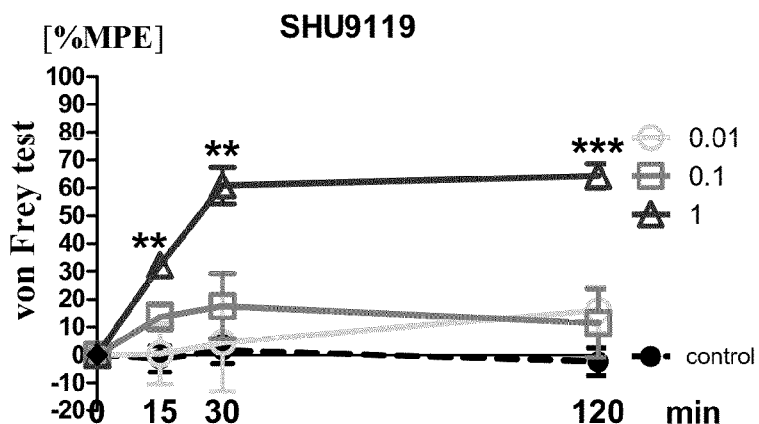
Figure 11:
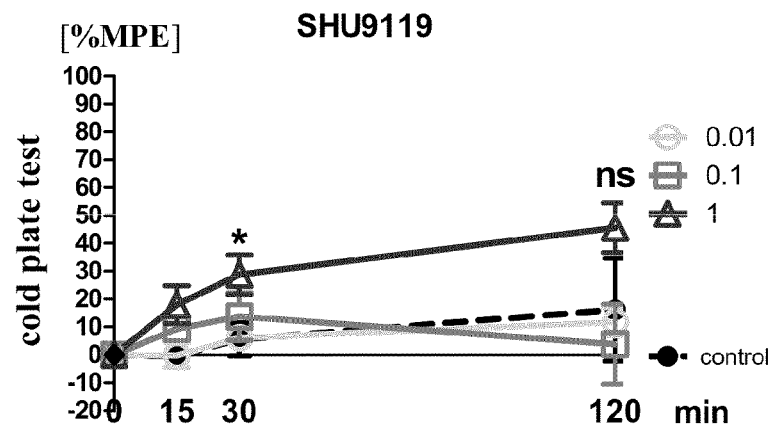
Figure 12:
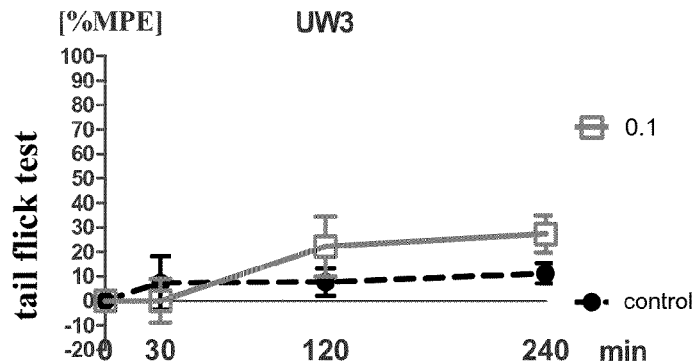
Figure 12:
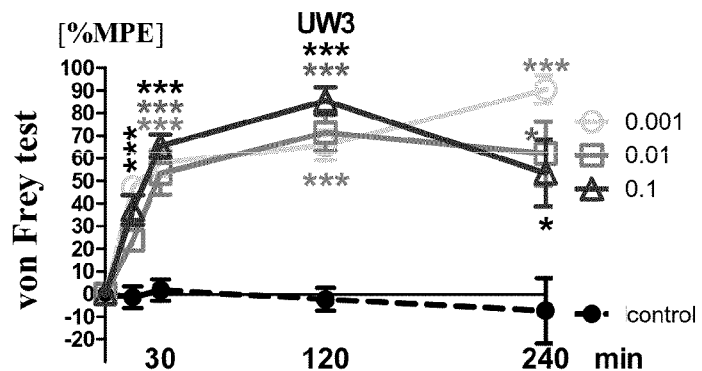
Figure 12:
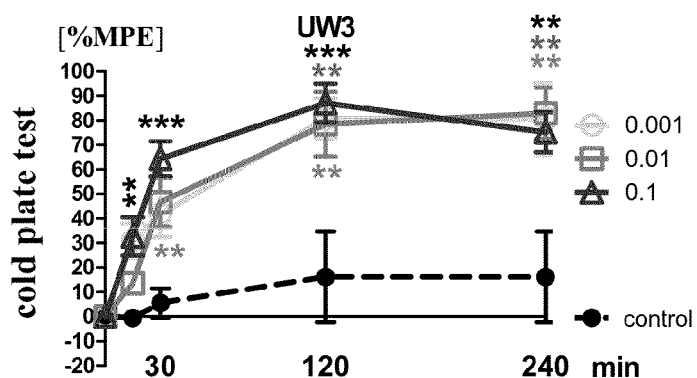
Figure 13:
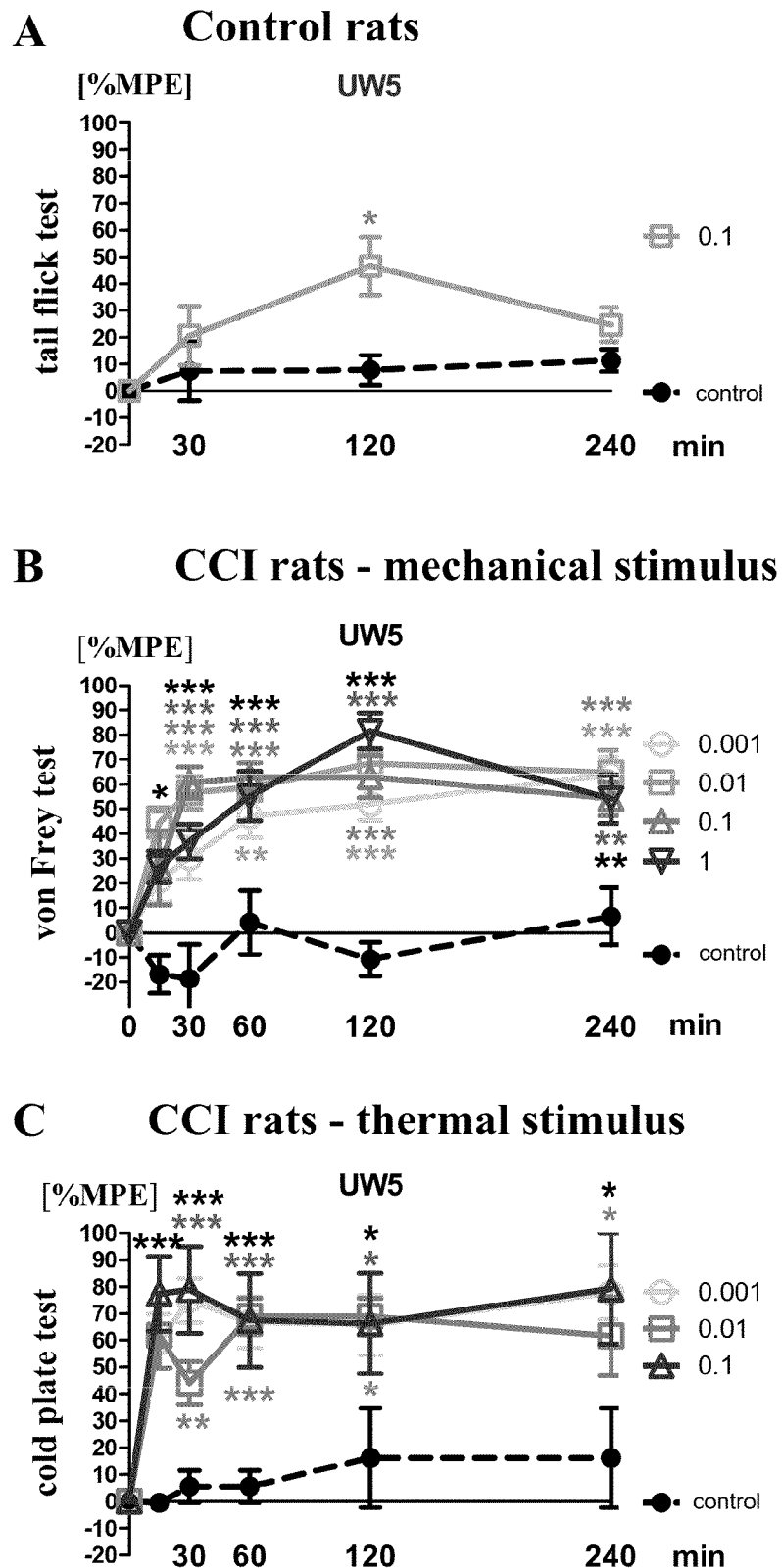

In the second stage of the pharmacological studies, the effect of the peripheral, intravenous administration of the hybrid peptidomimetics according to the invention (UW3, UW5) on the sensitivity to a mechanical stimulus (A) (von Frey test) and thermal stimulus (B) (cold plate test) threshold compared to a control group receiving water for injection was tested on mice in the neuropathy model (FIGS. 8 and 9). The studies were conducted at days 7-14 from the CCI procedure on mice at 15, 30 and 120 min after intravenous administration of the hybrid peptidomimetics UW3 and UW5 in the selected doses. They indicate the high analgesic efficiency of the hybrid peptidomimetics according to the invention (UW3, UW5) in the model of neuropathic pain also after peripheral administrations, which raises significantly their value as proposed medicinal substances due to possibility of their peripheral administration in the case of proposed clinical studies.

Discussion of the Results of the Second Stage Study on Rats

Wistar rats were subjected to cannulation for intrathecal administration by a method of Yaksh, T. L., Rudy, T. A., described in Physiol. Behay. 17, 1031-1036, 1976, and seven days after this procedure, a loose unilateral ligation of the right sciatic nerve (a chronic constriction injury, CCI) according to the model developed by Bennett and Xie (1988). After seven days from the CCI procedure, behavioral tests were conducted: the von Frey test and cold plate test to measure hypersensitivity to tactile and thermal stimuli, respectively. Hypersensitivity developed after injury of the nerve to two types of stimuli is a symptom of neuropathy. Behavioral tests were conducted at 15, 30, 120 and 240 minutes after intrathecal administration of the selected hybrid compound and its component parts: enkephalin/the compound UW1 (the opioid agonists) and SHU9119 (the MC4 receptor antagonist).

Discussion of the Results of the Study on Rats

The analgesic activity of the hybrid peptidomimetics UW3 and UW5 according to the invention in the control rats and in the rat model of neuropathic pain is shown on FIGS. 10-13. The activity graphs of the standard parent compounds (the opioid receptor agonist: UW1, MC4 receptor antagonist: SHU9119 and enkephalin) indicate their weak activity concerning both the healthy animals and the rat model of neuropathic pain. The novel hybrid peptidomimetics according to the invention (UW3 and UW5) exhibit also very weak activity in the control animals, but their analgesic activity strength in the rat model of neuropathic pain reaches maximum values in the conducted tests. The novel hybrid peptidomimetics powerfully counteract the hypersensitivity developed after the injury to both stimuli, meaning that their activity embraces both elements of the pathology developing after the nerve injury.

Efficiency of Hybrid Peptidomimetic Activity

Efficiency of activity of hybrid peptidomimetics according to the invention was characterized by providing the $ED_{50}$ parameter, i.e. a dose at which a half (50%) of the maximum effect of a given substance is reached or at which 50% of the individuals studied exhibit the expected effect. Results of the calculations are shown in Table 1 as activities of UW1, SHU9119 and the hybrid peptidomimetics according to the invention (UW3 and UW5) in control animals (testing the pain threshold, tail flick reflex) and in the model of neuropathic pain (testing sensitivity to mechanical stimuli-von Frey and to thermal stimuli-the cold plate 2° C.). The results were presented for doses in micrograms, at which a half (50%) of the maximum effect ($ED_{50}$) is reached. Calculation of the $ED_{50}$ value requires clear dose-dependent effects. Due to the lack of such an activity in healthy mice and after administration of SHU9119 this value could not be calculated. $ED_{50}$ values were not calculated for the reference compounds (UW2 UW4 UW6) due to their very weak and dose dependency-deprived analgesic activity.

TABLE 1

| | | Mice in the neuropathic pain model - a sciatic nerve injury (CCI) | |
| --- | --- | --- | --- |
| Compound tested | Control mice Tail flick test $ED_{50}$ (μg) | Von Frey test (allodynia) $ED_{50}$ (μg) | Cold plate (hyperalgesia) $ED_{50}$ (μg) |
| UW1 (Opioid agonist) | 0.03 (0.02-0.05) | 0.16 (0.1-0.25) | 9.3 (2.7-32) |
| SHU9119 (MC4 antagonist) | * | * | * |
| UW3 | * | 0.0004 (0.0001-0.002) | 0.008 (0.005-0.01) |
| UW5 | * | 0.02 (0.00003-15) | 0.2 (0.008-6.5) |

* no $ED_{50}$ could be calculated

On the basis of the data presented in the table it can be clearly seen that analgetic activity of the hybrid peptidomimetics according to the invention-UW3 and UW5, is attained after administration of much lower doses than in the case of the parent compound. The very low $ED_{50}$ values after administration of UW3 indicate its high biological activity. The high biological activity of UW3 permits to use low doses, meaning also indirectly a low dose of the opioid. This fact is significant in consideration of the chronic character of neuropathic pain and a need to continuous administration of drugs which in many cases leads to occurrence of undesired effects. The high biological activity of the hybrid peptidomimetics according to the invention- UW3 and UW5, guarantees a lower risk of undesired effects, with the high analgetic efficiency in neuropathic pain.

Conclusions

In conclusion, based on the above results of the preclinical studies conducted on the mouse and rat models of neuropathic pain, analgesic efficiency of the compounds according to the invention was shown in neuropathic pain. Thus, the compounds according to the invention constitute a promising starting point for the development of novel therapies for neuropathic pain, the treatment of which is still insufficient.

The invention claimed is:

1. A compound of the general formula:
$A^1$-$A^2$-$A^3$-$A^4$-X-Nle-cyclo[Asp-His-D-Nal(2')-Arg-Trp-Lys]-NH$_2$ wherein:
$A^1$ is a Tyr, DMT (2,6-dimethyltyrosine), or N-Me-Tyr (N-methyltyrosine) residue
$A^2$ is a D-Ala, D-Thr, D-Ser, D-Leu, D-Arg, D-Lys, or D-Pro residue
$A^3$ may be absent or is a Gly or Phe residue
$A^4$ is a Phe or Trp residue
X is -NH—(CH$_2$)$_n$—CO—, or —NH—(CH$_2$)$_n$—CO—NH—(CH$_2$)$_m$—CO—, wherein n and m are integers from 1 to 8;
or a pharmaceutically acceptable salt or hydrate thereof.

2. The compound of claim 1, characterized in that it is selected from the group consisting of:
Tyr-D-Ala-Gly-Phe-X-Nle-cyclo[Asp-His-D-Nal(2')-Arg-Trp-Lys]-NH$_2$;
Tyr-D-Thr-Gly-Phe-X-Nle-cyclo[Asp-His-D-Nal(2')-Arg-Trp-Lys]-NH$_2$;
Tyr-D-Leu-Gly-Phe-X-Nle-cyclo[Asp-His-D-Nal(2')-Arg-Trp-Lys]-NH$_2$;
Tyr-D-Ser-Gly-Phe-X-Nle-cyclo[Asp-His-D-Nal(2')-Arg-Trp-Lys]-NH$_2$;
DMT-D-Ala-Gly-Phe-X-Nle-cyclo[Asp-His-D-Nal(2')-Arg-Trp-Lys]-NH$_2$;
DMT-D-Thr-Gly-Phe-X-Nle-cyclo[Asp-His-D-Nal(2')-Arg-Trp-Lys]-NH$_2$;
DMT-D-Leu-Gly-Phe-X-Nle-cyclo[Asp-His-D-Nal(2')-Arg-Trp-Lys]-NH$_2$;
DMT-D-Ser-Gly-Phe-X-Nle-cyclo[Asp-His-D-Nal(2')-Arg-Trp-Lys]-NH$_2$;
wherein X is-NH—(CH$_2$)—CO—or—NH—(CH$_2$)$_n$—CO—NH—(CH$_2$)$_m$—CO—.

3. The compound of claim 2, characterized in that it is:
Tyr-D-Ala-Gly-Phe-NH—(CH$_2$)$_5$—CO-Nle-cyclo[Asp-His-D-Nal(2')-Arg-Trp-Lys]-NH$_2$ or
Tyr-D-Ala-Gly-Phe-NH—(CH$_2$)$_5$—CO—NH—(CH$_2$)$_5$—CO-Nle-cyclo[Asp-His-D-Nal(2')-Arg-Trp-Lysl-NH$_2$.

4. A pharmaceutical composition comprising as an active ingredient a compound as defined in claim 1.

5. A method of treatment of neuropathic pain wherein it involves administration of a compound of the general formula:
A1-A2-A3-A4-X-Nle-cyclo[Asp-His-D-Nal(2')-Arg-Trp-Lys]-NH2 wherein:
A1 is a Tyr, DMT (2,6-dimethyltyrosine), or N-Me-Tyr (N-methyltyrosine) residue
A2 is a D-Ala, D-Thr, D-Ser, D-Leu, D-Arg, D-Lys, or D-Pro residue
A3 may be absent or is a Gly or Phe residue
A4 is a Phe or Trp residue
X is-NH—(CH2)n-CO—, or —NH—(CH2)n-CO—NH—(CH2)m-CO—, wherein n and m are integers from 1 to 8;
or a pharmaceutically acceptable salt or hydrate thereof.

* * * * *